United States Patent
Blackwell et al.

(10) Patent No.: US 8,226,653 B2
(45) Date of Patent: Jul. 24, 2012

(54) SPINOUS PROCESS STABILIZATION DEVICES AND METHODS

(75) Inventors: Jonathan Blackwell, Cordova, TN (US); Aurelien Bruneau, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 214 days.

(21) Appl. No.: 12/772,789

(22) Filed: May 3, 2010

(65) Prior Publication Data
US 2010/0211101 A1  Aug. 19, 2010

Related U.S. Application Data

(63) Continuation of application No. 11/117,809, filed on Apr. 29, 2005, now Pat. No. 7,727,233.

(51) Int. Cl.
*A61F 2/44* (2006.01)
(52) U.S. Cl. ...................... 606/71; 623/17.11
(58) Field of Classification Search .......... 606/246–260, 606/70, 71; 623/17.11, 17.15, 17.16; 403/53, 403/54, 58, 59, 68, 73, 84
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |

(Continued)

FOREIGN PATENT DOCUMENTS

DE  2821678 A1  11/1979

(Continued)

OTHER PUBLICATIONS

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

(Continued)

*Primary Examiner* — Eduardo C Robert
*Assistant Examiner* — Tara Carter

(57) ABSTRACT

Devices and methods for supporting adjacent spinous processes include opposing plates movable toward one another along a cross post to contact opposite sides of each of the spinous processes, and a spacer member about the cross post contacting the adjacent surfaces of the spinous processes to resist movement of the spinous processes toward one another under spinal extension motion.

13 Claims, 9 Drawing Sheets

U.S. PATENT DOCUMENTS

| | | | |
|---|---|---|---|
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A * | 11/1999 | Jackson ........................ 606/252 |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B2 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |

| | | | | | |
|---|---|---|---|---|---|
| 6,981,975 B2 | 1/2006 | Michelson | 2006/0106397 A1 | 5/2006 | Lins |
| 7,011,685 B2 | 3/2006 | Arnin et al. | 2006/0111728 A1 | 5/2006 | Abdou |
| 7,041,136 B2 | 5/2006 | Goble et al. | 2006/0116690 A1 | 6/2006 | Pagano |
| 7,048,736 B2 | 5/2006 | Robinson et al. | 2006/0122620 A1 | 6/2006 | Kim |
| 7,070,598 B2 | 7/2006 | Lim et al. | 2006/0129239 A1 | 6/2006 | Kwak |
| 7,081,120 B2 | 7/2006 | Li et al. | 2006/0136060 A1 | 6/2006 | Taylor |
| 7,087,055 B2 | 8/2006 | Lim et al. | 2006/0142858 A1 | 6/2006 | Colleran et al. |
| 7,087,083 B2 | 8/2006 | Pasquet et al. | 2006/0149242 A1 | 7/2006 | Kraus et al. |
| 7,097,648 B1 | 8/2006 | Globerman et al. | 2006/0182515 A1 | 8/2006 | Panasik et al. |
| 7,097,654 B1 | 8/2006 | Freedland | 2006/0184247 A1 | 8/2006 | Edidin et al. |
| 7,101,375 B2 | 9/2006 | Zucherman et al. | 2006/0184248 A1 | 8/2006 | Edidin et al. |
| 7,163,558 B2 | 1/2007 | Senegas et al. | 2006/0195102 A1 | 8/2006 | Malandain |
| 7,201,751 B2 | 4/2007 | Zucherman et al. | 2006/0217726 A1 | 9/2006 | Maxy et al. |
| 7,217,293 B2 | 5/2007 | Branch, Jr. | 2006/0224159 A1 | 10/2006 | Anderson |
| 7,238,204 B2 | 7/2007 | Le Couedic et al. | 2006/0224241 A1 | 10/2006 | Butler et al. |
| 7,306,628 B2 | 12/2007 | Zucherman et al. | 2006/0235387 A1 | 10/2006 | Peterman |
| 7,335,203 B2 | 2/2008 | Winslow et al. | 2006/0235532 A1 | 10/2006 | Meunier et al. |
| 7,377,942 B2 | 5/2008 | Berry | 2006/0241601 A1 | 10/2006 | Trautwein et al. |
| 7,431,735 B2 | 10/2008 | Liu et al. | 2006/0241613 A1 | 10/2006 | Bruneau et al. |
| 7,442,208 B2 | 10/2008 | Mathieu et al. | 2006/0241643 A1 | 10/2006 | Lim et al. |
| 7,445,637 B2 | 11/2008 | Taylor | 2006/0241757 A1 | 10/2006 | Anderson |
| 7,458,981 B2 | 12/2008 | Fielding et al. | 2006/0247623 A1 | 11/2006 | Anderson et al. |
| 7,582,106 B2 | 9/2009 | Teitelbaum et al. | 2006/0247640 A1 | 11/2006 | Blackwell et al. |
| 7,604,652 B2 | 10/2009 | Arnin et al. | 2006/0264938 A1 | 11/2006 | Zucherman et al. |
| 7,611,316 B2 | 11/2009 | Panasik et al. | 2006/0271044 A1 | 11/2006 | Petrini et al. |
| 7,621,950 B1 | 11/2009 | Globerman et al. | 2006/0271049 A1 | 11/2006 | Zucherman et al. |
| 7,658,752 B2 | 2/2010 | Labrom et al. | 2006/0271061 A1 | 11/2006 | Beyer et al. |
| 7,749,252 B2 | 7/2010 | Zucherman et al. | 2006/0282075 A1 | 12/2006 | Labrom et al. |
| 7,771,456 B2 | 8/2010 | Hartman et al. | 2006/0282079 A1 | 12/2006 | Labrom et al. |
| 7,862,615 B2 | 1/2011 | Carli et al. | 2006/0293662 A1 | 12/2006 | Boyer, II et al. |
| 7,901,430 B2 | 3/2011 | Matsuura et al. | 2006/0293663 A1 | 12/2006 | Walkenhorst et al. |
| 2001/0016743 A1 | 8/2001 | Zucherman et al. | 2007/0005064 A1 | 1/2007 | Anderson et al. |
| 2002/0143331 A1 | 10/2002 | Zucherman et al. | 2007/0010813 A1 | 1/2007 | Zucherman et al. |
| 2003/0040746 A1 | 2/2003 | Mitchell et al. | 2007/0032790 A1 | 2/2007 | Aschmann et al. |
| 2003/0045940 A1 | 3/2003 | Eberlein et al. | 2007/0043362 A1 | 2/2007 | Malandain et al. |
| 2003/0065330 A1* | 4/2003 | Zucherman et al. ............ 606/61 | 2007/0043363 A1 | 2/2007 | Malandain et al. |
| 2003/0153915 A1 | 8/2003 | Nekozuka et al. | 2007/0073289 A1 | 3/2007 | Kwak et al. |
| 2004/0010312 A1 | 1/2004 | Enayati | 2007/0100340 A1 | 5/2007 | Lange et al. |
| 2004/0010316 A1 | 1/2004 | William et al. | 2007/0123861 A1 | 5/2007 | Dewey et al. |
| 2004/0087947 A1 | 5/2004 | Lim et al. | 2007/0142915 A1 | 6/2007 | Altarac et al. |
| 2004/0097931 A1 | 5/2004 | Mitchell | 2007/0151116 A1 | 7/2007 | Malandain |
| 2004/0106995 A1 | 6/2004 | LeCouedic et al. | 2007/0162000 A1 | 7/2007 | Perkins |
| 2004/0117017 A1 | 6/2004 | Pasquet et al. | 2007/0167945 A1 | 7/2007 | Lange et al. |
| 2004/0133204 A1 | 7/2004 | Davies | 2007/0173822 A1 | 7/2007 | Bruneau et al. |
| 2004/0133280 A1 | 7/2004 | Trieu | 2007/0173823 A1 | 7/2007 | Dewey et al. |
| 2004/0158248 A1 | 8/2004 | Ginn | 2007/0191833 A1 | 8/2007 | Bruneau et al. |
| 2004/0167625 A1 | 8/2004 | Beyar et al. | 2007/0191834 A1 | 8/2007 | Bruneau et al. |
| 2004/0199255 A1 | 10/2004 | Mathieu et al. | 2007/0191837 A1 | 8/2007 | Trieu |
| 2004/0260397 A1 | 12/2004 | Lambrecht et al. | 2007/0191838 A1 | 8/2007 | Bruneau et al. |
| 2005/0010293 A1 | 1/2005 | Zucherman et al. | 2007/0198091 A1 | 8/2007 | Boyer et al. |
| 2005/0033434 A1 | 2/2005 | Berry | 2007/0225807 A1 | 9/2007 | Phan et al. |
| 2005/0049708 A1 | 3/2005 | Atkinson et al. | 2007/0233068 A1 | 10/2007 | Bruneau et al. |
| 2005/0085814 A1 | 4/2005 | Sherman et al. | 2007/0233074 A1 | 10/2007 | Anderson et al. |
| 2005/0143827 A1 | 6/2005 | Globerman et al. | 2007/0233076 A1 | 10/2007 | Trieu |
| 2005/0165398 A1 | 7/2005 | Reiley | 2007/0233081 A1 | 10/2007 | Pasquet et al. |
| 2005/0203512 A1* | 9/2005 | Hawkins et al. ................ 606/61 | 2007/0233089 A1 | 10/2007 | DiPoto et al. |
| 2005/0203519 A1 | 9/2005 | Harms et al. | 2007/0250060 A1 | 10/2007 | Anderson et al. |
| 2005/0203624 A1 | 9/2005 | Serhan et al. | 2007/0270823 A1 | 11/2007 | Trieu et al. |
| 2005/0228391 A1 | 10/2005 | Levy et al. | 2007/0270824 A1 | 11/2007 | Lim et al. |
| 2005/0245937 A1 | 11/2005 | Winslow | 2007/0270825 A1 | 11/2007 | Carls et al. |
| 2005/0261768 A1 | 11/2005 | Trieu | 2007/0270826 A1 | 11/2007 | Trieu et al. |
| 2005/0267579 A1 | 12/2005 | Reiley et al. | 2007/0270827 A1 | 11/2007 | Lim et al. |
| 2005/0273166 A1 | 12/2005 | Sweeney | 2007/0270828 A1 | 11/2007 | Bruneau et al. |
| 2005/0288672 A1 | 12/2005 | Ferree | 2007/0270829 A1 | 11/2007 | Carls et al. |
| 2006/0004447 A1 | 1/2006 | Mastrorio et al. | 2007/0270834 A1 | 11/2007 | Bruneau et al. |
| 2006/0004455 A1 | 1/2006 | Leonard et al. | 2007/0270874 A1 | 11/2007 | Anderson |
| 2006/0015181 A1 | 1/2006 | Elberg | 2007/0272259 A1 | 11/2007 | Allard et al. |
| 2006/0064165 A1 | 3/2006 | Zucherman et al. | 2007/0276368 A1 | 11/2007 | Trieu et al. |
| 2006/0084983 A1 | 4/2006 | Kim | 2007/0276369 A1 | 11/2007 | Allard et al. |
| 2006/0084985 A1 | 4/2006 | Kim | 2007/0276493 A1 | 11/2007 | Malandain et al. |
| 2006/0084987 A1 | 4/2006 | Kim | 2007/0276496 A1 | 11/2007 | Lange et al. |
| 2006/0084988 A1 | 4/2006 | Kim | 2007/0276497 A1 | 11/2007 | Anderson |
| 2006/0085069 A1 | 4/2006 | Kim | 2007/0282443 A1 | 12/2007 | Globerman et al. |
| 2006/0085070 A1 | 4/2006 | Kim | 2008/0021457 A1 | 1/2008 | Anderson et al. |
| 2006/0085074 A1 | 4/2006 | Raiszadeh | 2008/0021460 A1 | 1/2008 | Bruneau et al. |
| 2006/0089654 A1 | 4/2006 | Lins et al. | 2008/0058934 A1 | 3/2008 | Malandain et al. |
| 2006/0089719 A1 | 4/2006 | Trieu | 2008/0097446 A1 | 4/2008 | Reiley et al. |
| 2006/0095136 A1 | 5/2006 | McLuen | 2008/0114357 A1 | 5/2008 | Allard et al. |
| 2006/0106381 A1 | 5/2006 | Ferree et al. | 2008/0114358 A1 | 5/2008 | Anderson et al. |

| | | | |
|---|---|---|---|
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2010/0121379 A1 | 5/2010 | Edmond | |
| 2010/0204732 A1 | 8/2010 | Aschmann et al. | |

FOREIGN PATENT DOCUMENTS

| | | | |
|---|---|---|---|
| DE | 3922044 A1 | 2/1991 | |
| DE | 4012622 C1 | 7/1991 | |
| EP | 0322334 B1 | 2/1992 | |
| EP | 0767636 B1 | 1/1999 | |
| EP | 1004276 A1 | 5/2000 | |
| EP | 1011464 B1 | 6/2000 | |
| EP | 1138268 A1 | 10/2001 | |
| EP | 1148850 B1 | 10/2001 | |
| EP | 1148851 B1 | 10/2001 | |
| EP | 1302169 A1 | 4/2003 | |
| EP | 1330987 A1 | 7/2003 | |
| EP | 1552797 A2 | 7/2005 | |
| EP | 1854433 A1 | 11/2007 | |
| EP | 1905392 A1 | 4/2008 | |
| EP | 1982664 A1 | 10/2008 | |
| FR | 2623085 A1 | 5/1989 | |
| FR | 2625097 A1 | 6/1989 | |
| FR | 2681525 A1 | 3/1993 | |
| FR | 2700941 A1 | 8/1994 | |
| FR | 2703239 A1 | 10/1994 | |
| FR | 2707864 A1 | 1/1995 | |
| FR | 2717675 A1 | 9/1995 | |
| FR | 2722087 A1 | 1/1996 | |
| FR | 2722088 A1 | 1/1996 | |
| FR | 2724554 A1 | 3/1996 | |
| FR | 2725892 A1 | 4/1996 | |
| FR | 2730156 A1 | 8/1996 | |
| FR | 2731643 A1 | 9/1996 | |
| FR | 2775183 A1 | 8/1999 | |
| FR | 2799948 A1 | 4/2001 | |
| FR | 2816197 A1 | 5/2002 | |
| JP | 02-224660 | 9/1990 | |
| JP | 09-075381 | 3/1997 | |
| JP | 2003079649 | 3/2003 | |
| SU | 988281 | 1/1983 | |
| SU | 1484348 A1 | 6/1989 | |
| WO | 94/26192 | 11/1994 | |
| WO | 94/26195 | 11/1994 | |
| WO | 97/18769 | 5/1997 | |
| WO | 98/20939 | 5/1998 | |
| WO | 99/26562 | 6/1999 | |
| WO | 00/44319 | 8/2000 | |
| WO | 01/54598 A1 | 8/2001 | |
| WO | 03/057055 A1 | 7/2003 | |
| WO | 2004/047689 A1 | 6/2004 | |
| WO | 2004/047691 A1 | 6/2004 | |
| WO | 2004/084743 A1 | 10/2004 | |
| WO | 2004/084768 A2 | 10/2004 | |
| WO | 2004/110300 A2 | 12/2004 | |
| WO | 2005/009300 A1 | 2/2005 | |
| WO | 2005/011507 A1 | 2/2005 | |
| WO | 2005/044118 A1 | 5/2005 | |
| WO | 2005/048856 A1 | 6/2005 | |
| WO | 2005/110258 A1 | 11/2005 | |
| WO | 2006/064356 A1 | 6/2006 | |
| WO | 2007/034516 A1 | 3/2007 | |
| WO | 2007052975 A1 | 5/2007 | |
| WO | 2009/083276 A1 | 7/2009 | |
| WO | 2009/083583 A1 | 7/2009 | |
| WO | 2009/098536 A1 | 8/2009 | |

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienné," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societá di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Francaise, Paris, France.

Senegas, "La Ligamentoplastie Inter Vertébrale Lombaire, Alternative a L'Arthrodèse," La Revue de Medéecine Orthopédique, Jun. 1990, pp. 33-35, No. 20.

Senegas, "La Ligamentoplastie Intervertébrale, Alternative à L'arthrodése dans le Traitement des Instabilités Dégénératives," Acta Othopaedica Belgica, 1991, pp. 221-226, vol. 57, Suppl. 1.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

Anasetti et al., "Spine Stability After Implantation of an Interspinous Device: An in Vitro and Finite Element Biomechanical Study," J. Neurosurg. Spine, Nov. 2010, vol. 13, pp. 568-575.

Bellini et al., "Biomechanics of the Lumbar Spine Afer Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

\* cited by examiner

SPINOUS PROCESS STABILIZATION DEVICES AND METHODS

This application is a continuation of prior application Ser. No. 11/117,809, filed 29 Apr. 2005, the entirety of which is incorporated herein by reference.

BACKGROUND

Spinal stabilization procedures are performed and include placement of devices between vertebral bodies in the disc space or along the spinal column. For example, varieties of inter-body fusion devices are widely used following partial or total discectomies to fuse adjacent vertebrae. Artificial disc devices can be placed in the disc space if motion preservation is desired. Still other stabilization devices contemplate the attachment of plates, rods or tethers extradiscally along the vertebrae. Still others are positioned between spinous processes. One example is shown in U.S. Patent Application Publication No. 2003/0216736, which is incorporated herein by reference. There remains a need for devices for spinal stabilization through attachment to the spinous processes along one or more vertebral levels.

SUMMARY

Devices and methods for supporting adjacent spinous processes include opposing plates movable toward one another along a cross post to contact opposite sides of each of the spinous processes, and a member about the cross post contacting the adjacent surfaces of the spinous processes to resist movement of the spinous processes toward one another under spinal extension motion.

According to one aspect, there is provided an implantable device for stabilization of spinous processes. The device includes first and second spaced plates, the first plate having a surface facing a surface of the second plate. A post connected to each of the plates extends from the facing surface of the first plate to the facing surface of the second plate. The connection of the post to the second plate can be adjustable to enable a change of spacing between the first plate and the second plate. A spacer member can be non-rotatably positioned about the post. The spacer member is sized to extend between and contact adjacent surfaces of the spinous processes.

In another aspect, an implantable device for stabilization of spinous processes includes first and second spaced plates each having clamping surfaces facing one another. A post is connected to each of the plates and extends from and is pivotal relative to the clamping surface of the first plate. The connection of the post to the second plate is adjustable to enable changing the spacing between the first plate and the second plate. A spacer member can be positioned about the post. The spacer member is sized to extend between and contact adjacent superior and inferior surfaces of the spinous processes with the clamping surfaces positioned against opposite sides of the spinous processes.

According to another aspect, a method for stabilizing spinous processes of a spinal column comprises: selecting a spacer member from a set of spacer members, the selected spacer member providing a desired fit between adjacent spinous processes; engaging a first plate along a first side of the adjacent spinous processes; positioning the spacer member along a post extending from the first plate and between the adjacent spinous processes, the spacer member extending between and limiting extension movement of the adjacent spinous processes; and engaging a second plate along a second side of the adjacent spinous process with the spacer member between the first and second plates.

These and other aspects will be discussed further below.

DESCRIPTION OF THE ILLUSTRATED EMBODIMENTS

Figure 1:
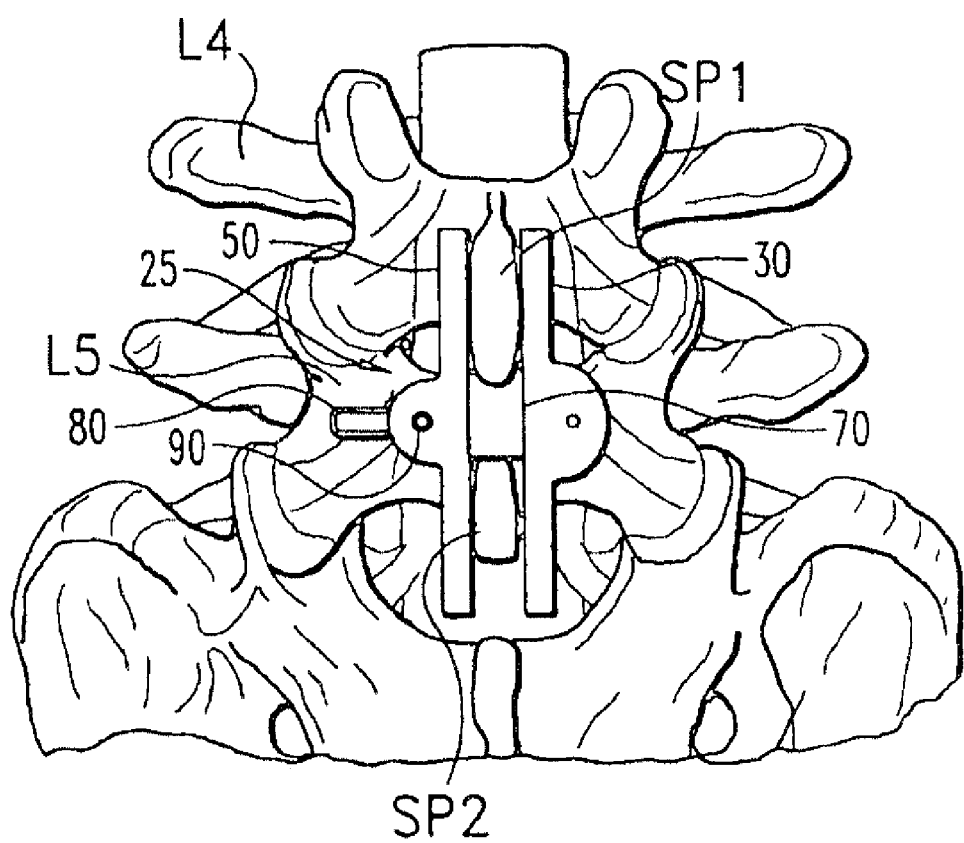
FIG. 1 is a posterior view of a portion of the spine with a device positioned between adjacent spinous processes.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 2:
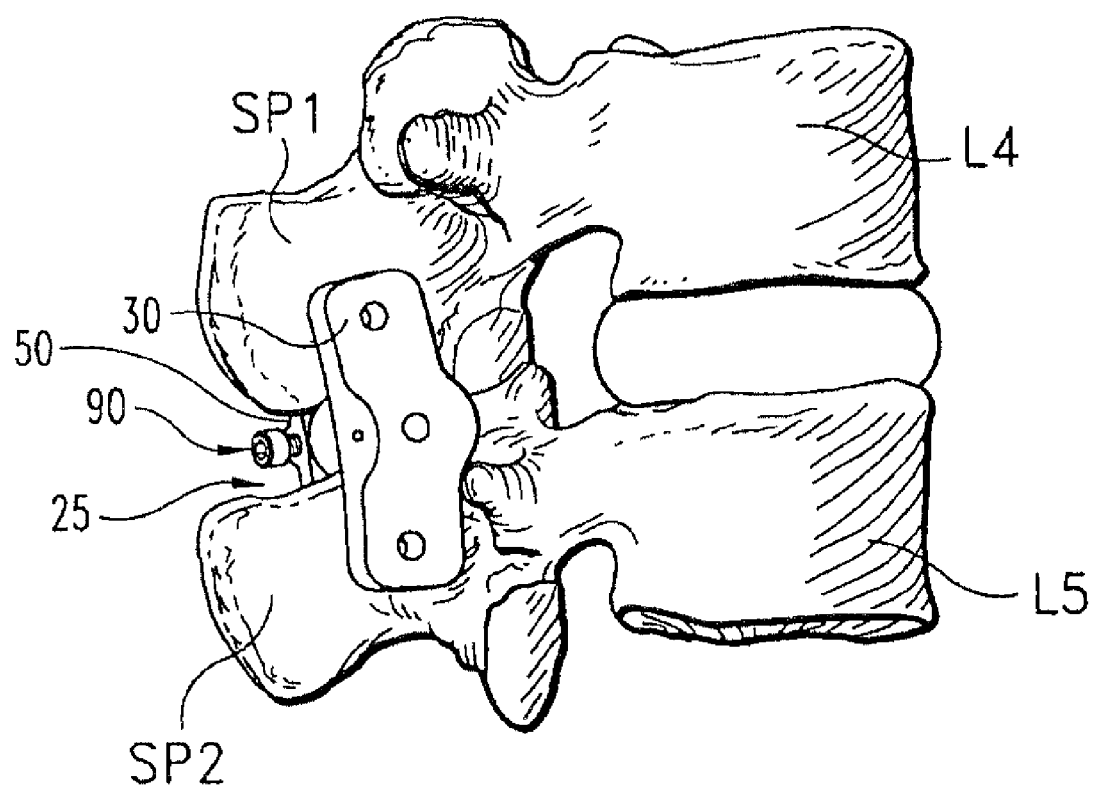
FIG. 2 is a laterally oriented view of the device and spine portion of FIG. 1.

In FIGS. 1 and 2 there is shown a device 25 engaged to the spinal processes SP1 and SP2 of the L4 and L5 vertebrae. While vertebrae L4 and L5 are shown, it is contemplated that device 25 can be engaged to adjacent spinous processes at any vertebral level of the spinal column. The device may also be adapted to extend along multiple vertebral levels, and it is also contemplated that individual devices may be employed at multiple vertebral levels.

Device 25 includes a first plate 30, a second plate 50 and a spacer member 70 therebetween. First and second plates 30, 50 are movable toward one another along a cross post 80 into clamping engagement with spinous processes SP1, SP2. Locking member 90 can engage cross post 80 to maintain a desired relative positioning between first and second plates 30, 50. A spacer member 70 is positioned along cross post 80, and extends between adjacent super and inferior surfaces of the spinous processes SP1 and SP2.

Engagement of plates 30, 50 to the spinous processes SP1, SP2 resists movement of the spinous processes SP1, SP2 toward and away from one another as a result of spinal extension and flexion, respectively, or as a result of any other movement or condition. Spacer member 70 extends between plates 30, 50 and also between spinous processes SP1, SP2 to resist movement of the spinous processes toward one another as a result of spinal extension. Spacer member 70 can also provide support of the vertebrae to maintain or provide post-operative distraction between the spinous processes SP1 and SP2.

Figure 3:
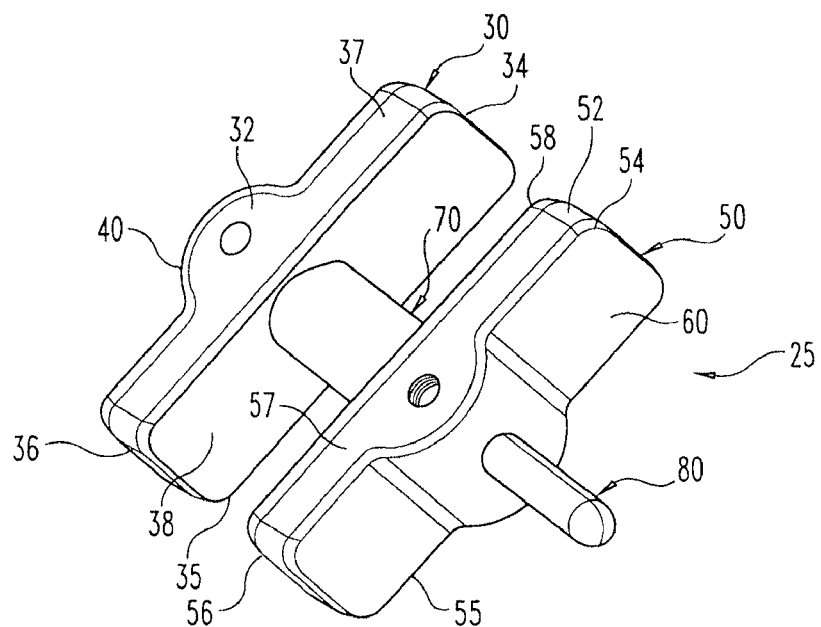
FIG. 3 is a perspective view of the device of FIG. 1.

A perspective view of device 25 is shown in FIG. 3 with plates 30, 50 switched in positioning relative to their orientation in FIGS. 1 and 2, and also with cross post 80 extending in the opposite direction from its FIG. 1 direction. In addition, locking member 90 is removed. First plate 30 includes an elongated body 32 extending between a cephalad end 34 and a caudal end 36, and also between an anterior side 35 and a posterior side 37. Body 32 can be rounded about ends 34, 36 and also sides 35, 37 to remove any abrupt transitions between surfaces that may contact and cause irritation in adjacent tissue and/or neural elements.

First plate 30 further includes a clamping surface 38 and an opposite outer surface 40. Clamping surface 38 is positionable against the sides of the respective adjacent spinous processes SP1 and SP2 to provide frictional engagement therewith. As discussed further below, cross post 80 includes one end secured to first plate 30 and extends transversely thereto from clamping surface 38 toward second plate 50.

Second plate 50 is positioned about and movable along cross post 80 and securable in position thereto with locking member 90. Second plate 50 includes an elongated body 52 extending between a cephalad end 54 and a caudal end 56, and also between an anterior side 55 and a posterior side 57. Body 52 can be rounded about ends 54, 56 and also sides 55, 57 to remove any abrupt transitions between surfaces that may contact and irritate adjacent tissue and/or neural elements.

Figure 4:
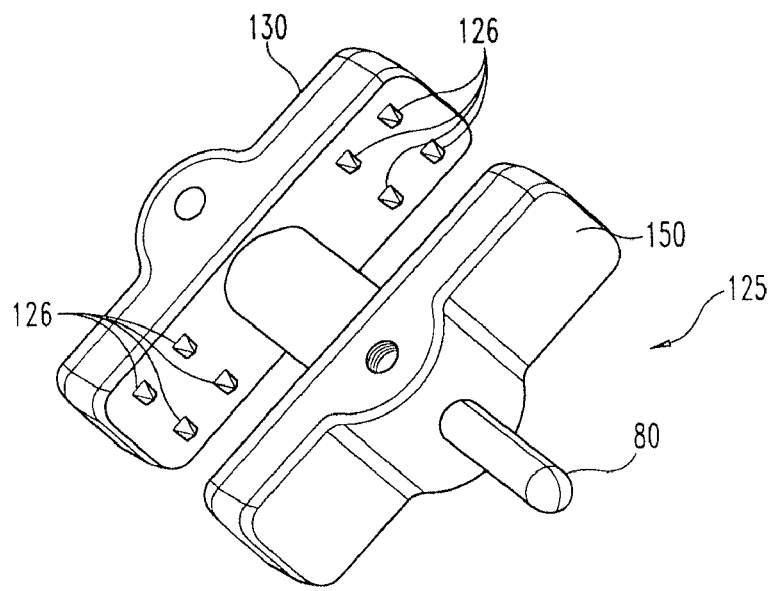
FIG. 4 is a perspective view of another embodiment device.

Second plate 50 further includes a clamping surface 58 and an opposite outer surface 60. Clamping surface 58 is positionable against the sides of the respective adjacent spinous processes SP1 and SP2 to provide frictional engagement therewith. In another embodiment, a substantially similar spinous process stabilization device 125 is shown in FIG. 4. In device 125, spikes 126 extend from a clamping surface of first plate 130 to embed in the bony structure of the spinous processes. In another embodiment device 125 shown in FIG. 4, spikes (not shown in second plate 150) extend from a clamping surface of second plate 150 to embed in the bony structure of the spinous processes. Other surface treatments are also contemplated, including ridges, knurlings, peaks and valleys, teeth, and etchings, for example.

Figure 5:
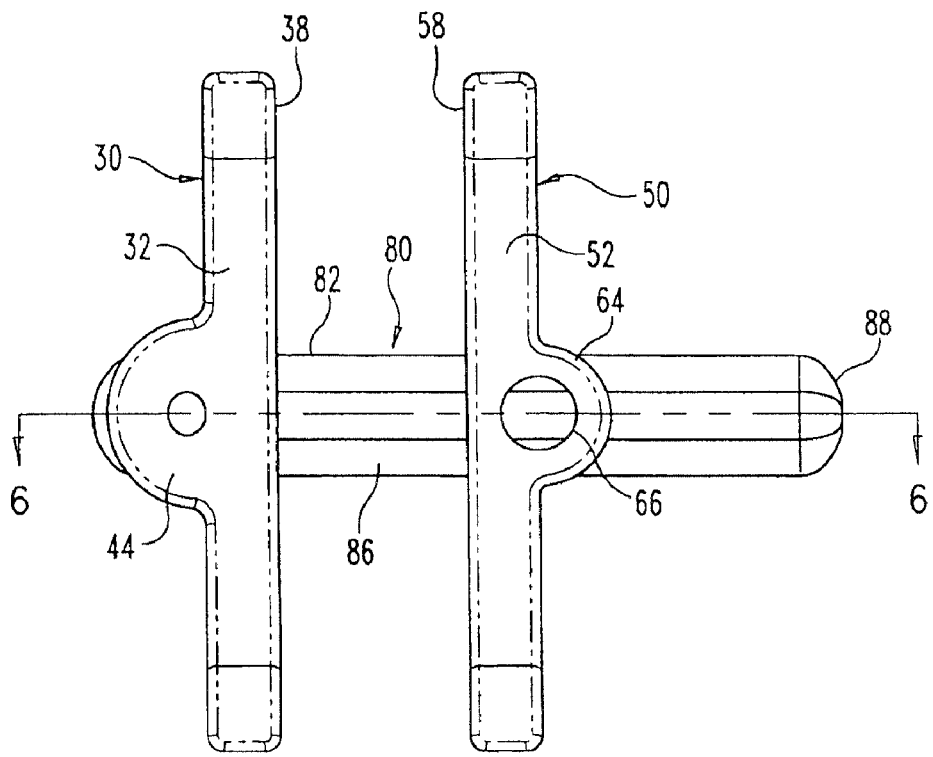
FIG. 5 is an elevation view of the device with the central spacer member removed.
Figure 6:
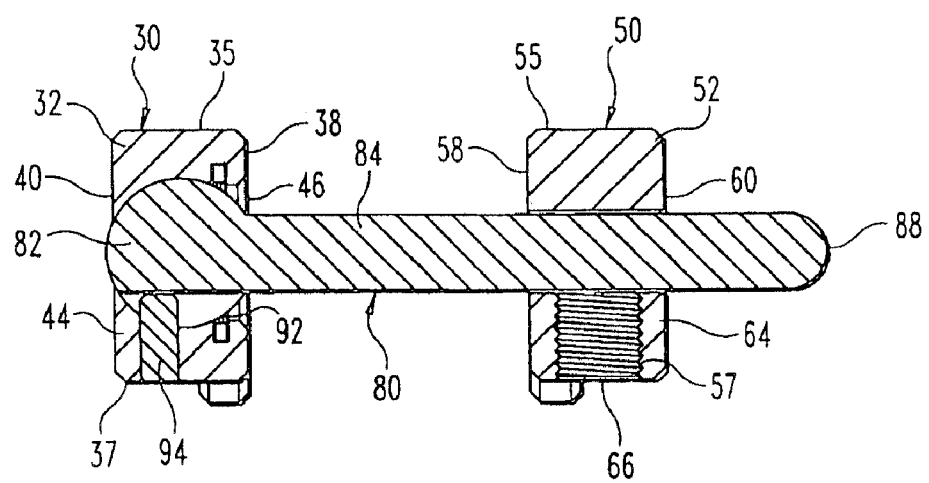
FIG. 6 is a section view along line 6-6 of FIG. 5.
Figure 7:
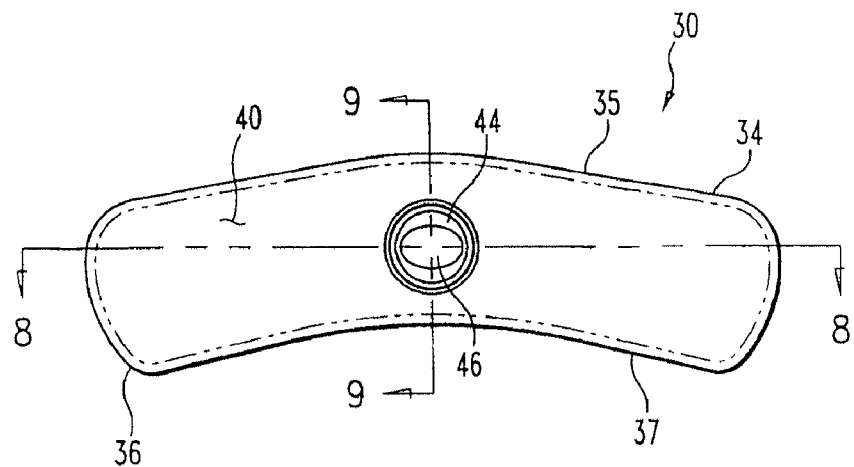
FIG. 7 is an elevation view of a first plate comprising a portion of the device.
Figure 8:
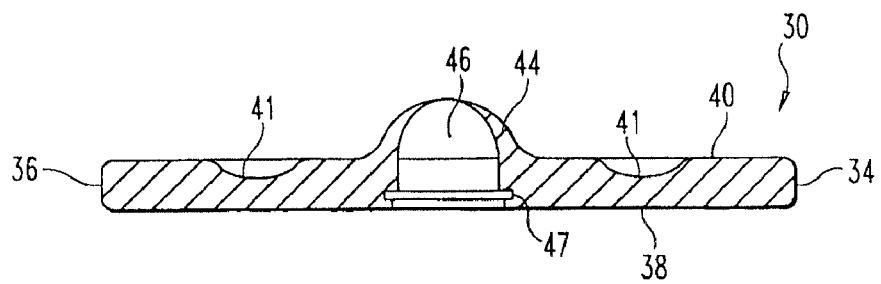
FIG. 8 is a section view along line 8-8 of FIG. 7.
Figure 9:
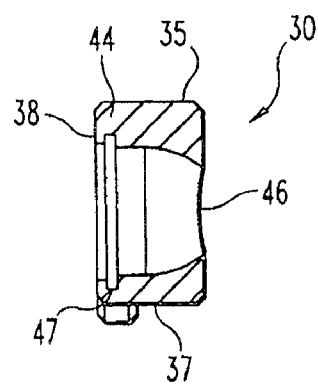
FIG. 9 is a section view along line 9-9 of FIG. 7.

Device 25 is further shown in FIGS. 5 and 6 without spacer member 70. First plate 30, shown in isolation in FIGS. 7-9, includes a central receiving portion 44 that defines a receptacle 46 that receives a head 82 of cross post 80 therein. A retaining member 92 is received in circumferential groove 47 and extends about receptacle 46 and the underside of head 82 to capture head 82 in receptacle 46. In one embodiment, head 82 is pivotal in receptacle 46, allowing various angular positions of an elongated shaft 84 extending through retaining member 92 from head 82 to a terminal end 88. The underside of head 82 can be seated upon retaining member 92 to prevent plates 30, 50 from moving away from one another. Retaining member 92 can be in the form of a C-shaped ring or any other form suitable to retain head 82 in receptacle 46.

Figure 13:
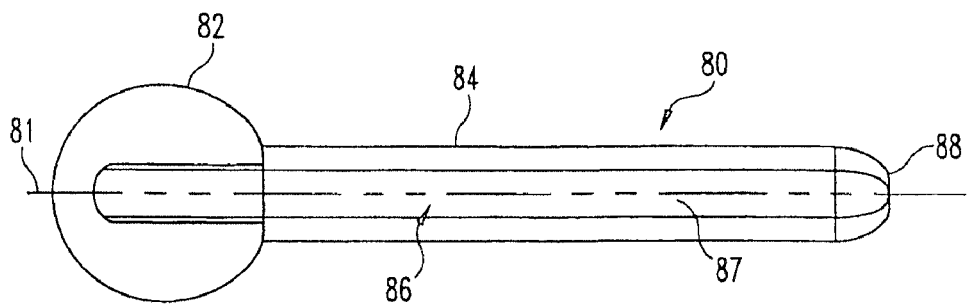
FIG. 13 is an elevation view of a cross post comprising a portion of the device.
Figure 14:
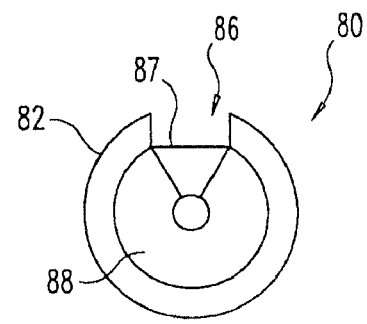
FIG. 14 is an end view of the cross post of FIG. 13.

As further shown in FIGS. 13-14, cross post 80 includes a keyway 86 extending therealong from head 82 to terminal end 88. Keyway 86 forms a channel at least in head 82 to receive pin 94 and resist cross post 80 from rotating about its longitudinal axis 81 in receptacle 46. Keyway 86 includes a flat surface portion 87 along shaft 84 that extends from head 82 to a terminal end 88. In another form, shaft 84 of cross post 80 includes a circular cross-section with no keyway therealong. Such an embodiment may be employed, for example, when it is desired to employ spacer members rotatable about cross post 80, as discussed further below.

Figure 10:
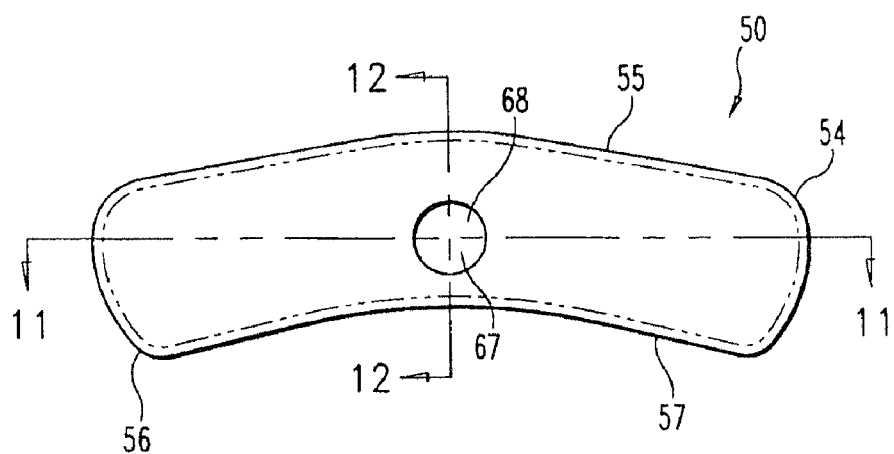
FIG. 10 is an elevation view of a second plate comprising a portion of the device.
Figure 11:
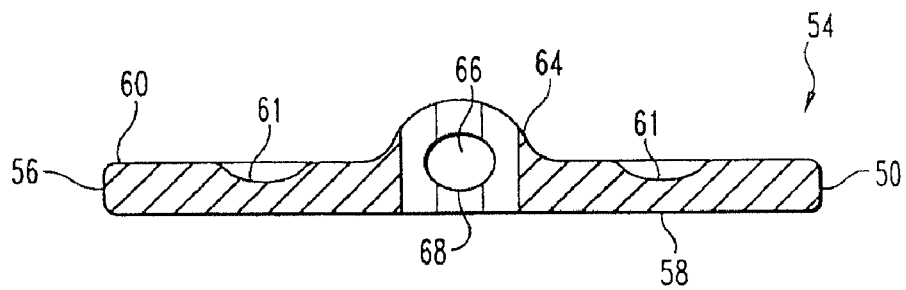
FIG. 11 is a section view along line 11-11 of FIG. 10.
Figure 12:
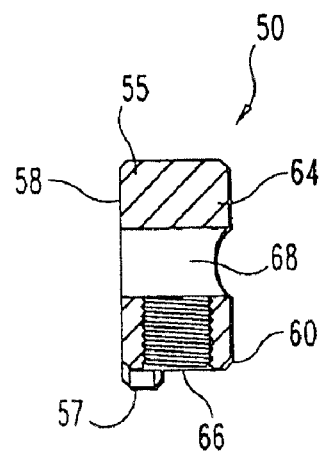
FIG. 12 is a section view along line 12-12 of FIG. 10.

Second plate 50, shown in isolation in FIGS. 10-12, includes a central receiving portion 64 that defines a receptacle 66 in communication with a through-bore 68. Through-bore 68 extends between and opens at clamping surface 58 and outer surface 60. Receptacle 66 is formed through central receiving portion 64 and is in communication with through-bore 68 and opens at posterior side 57. In the illustrated embodiment, receptacle 66 is threaded and threadingly engages an externally threaded locking member 90. Locking member 90 is movable along receptacle 66 into and out of engagement with keyway 86 of cross post 80 to secure second plate 50 in a desired position and relative spacing from first plate 30 along cross post 80.

Post 80 is positionable through through-bore 68 to allow securement of second plate 50 thereto. In the illustrated embodiment, through-bore 68 includes a keypath 67 that interacts with keyway 86 to prevent second plate 50 from rotating about cross post 80. The flats on the cross post 80 and through-bore 68 are interruptions in the circular form of the post and bore that interfit to prevent plate 50 from rotating. The post and bore could be of some other cross sectional shape providing a slip fit but avoiding rotation of the locking plate relative to the post. For example, polygonal or interdigitating key and key-way shapes could be used.

First and second plates 30, 50 can be curved between their respective upper and lower ends. For example, anterior sides 35, 55 are convexly curved to provide an anatomical fit between the spinous processes. Concavely curved posterior sides 37, 57 minimize posterior protrusion of plates 50, 70 in the region between the spinous process. Outer surfaces 40, 60 of first and second plates 30, 50 can further include reliefs 41, 61 to facilitate placement and retention of ends of a compression tool (not shown) that is operable to apply a compression force to move the plates into clamping engagement on the spinal processes.

The central receiving portions 44, 64 of plates 30, 50 provide an area of increased thickness of the plates to accommodate attachment of the respective portions of the cross post 80 and locking member 90. Other embodiments contemplate that the plates 30, 50 have a constant thickness along their respective lengths. In other embodiments, the plates 30, 50 may include longitudinal ribs to increase stiffness, or through holes to allow attachment of tethering or other supplemental spinal stabilization or attachment devices.

Figure 15:
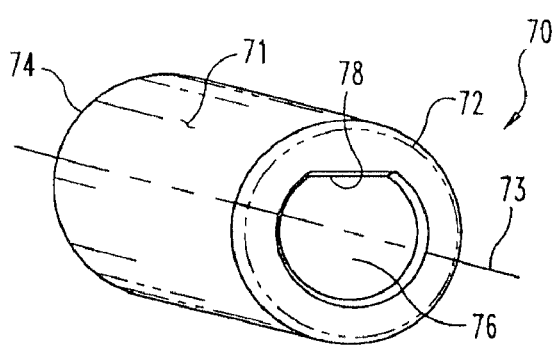
FIG. 15 is a perspective view of one embodiment spacer member.

Various embodiments of spacer members are shown in FIGS. 15-21. In FIG. 15 spacer member 70 includes a cylindrical body extending along a longitudinal axis 73. The body includes an outer surface 71 defining a circular shape in cross-section when viewed orthogonally to axis 73. A passage 76 extends along axis 73 between opposite ends 72, 74 and is sized and shaped to slidably receive cross post 80 therethrough. A keyed portion 78 is provided along one side of passage 76 that is positionable in contact with keyway 86 of cross post 80. Keyed portion 78 interacts with keyway 86 to prevent spacer member 70 from rotating about cross post 80.

Figure 16:
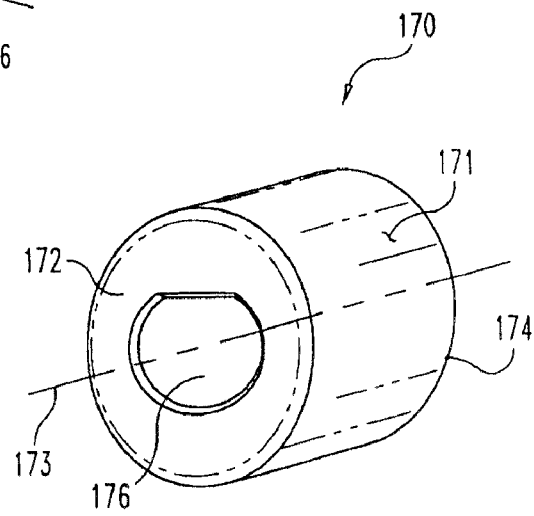
FIG. 16 is a perspective view of another embodiment spacer member.

In FIG. 16 another embodiment spacer member 170 is provided that is similar to spacer member 70 and includes a cylindrical body extending along longitudinal axis 173 between opposite ends 172, 174. The body includes an outer surface 171 extending thereabout that defines an oval shape in cross-section orthogonally to longitudinal axis 173. A passage 176 extends along axis 173 and is sized and shaped to slidingly receive cross post 80 therein. The elongated or maximum height portions of the oval can be oriented toward the respective inferior and superior spinous process surfaces. This orients the reduced width portion of the oval shape in the anterior-posterior direction to minimize intrusion into the adjacent tissue while maximizing the height between the spinous processes.

Figure 17:
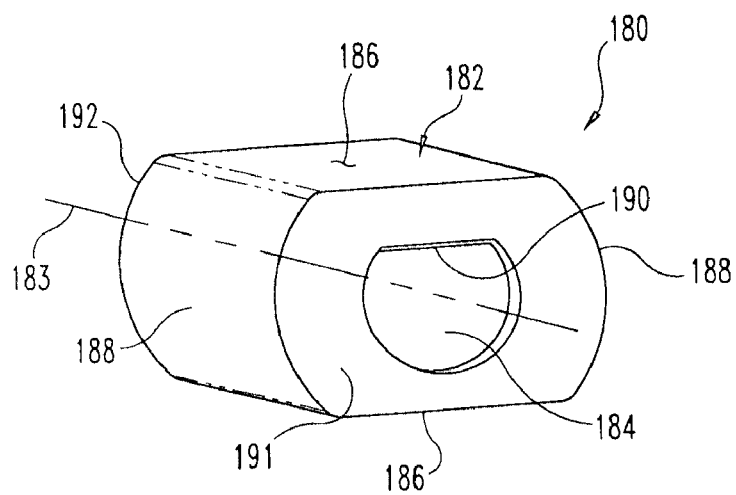
FIG. 17 is a perspective view of another embodiment spacer member.

FIG. 17 shows another embodiment spacer member 180 having a cylindrical body 182 extending along a longitudinal axis 183. The body includes a generally rectangular outer surface profile in cross-section viewed orthogonally to longitudinal axis 183. A passage 184 extends along axis 183 between opposite flat ends 191, 192. The outer surface profile includes convexly curved anterior and posterior walls 188 extending between planar upper and lower surfaces 186. Passage 184 can include a keyed portion 190 to prevent rotation of spacer member 180 about cross post 80 and to ensure proper alignment during assembly.

Figure 18:
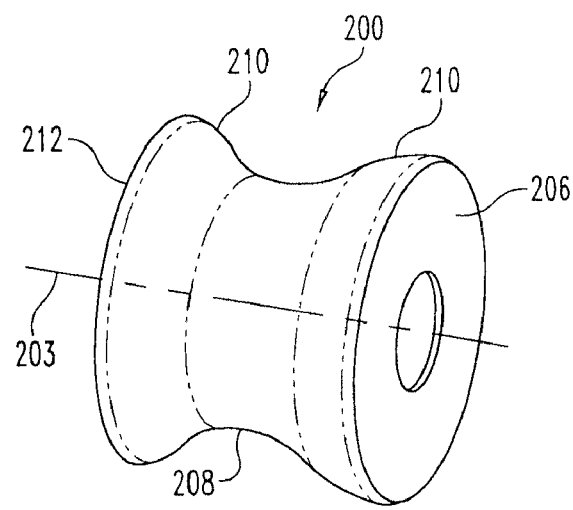
FIG. 18 is a perspective view of another embodiment spacer member.

FIG. 18 shows another embodiment spacer member 200 having a cylindrical body extending along longitudinal axis 203. The body includes an outer shape in the form of an hourglass extending along longitudinal axis 203. A passage 204 extends along axis 203 between opposite flat ends 206, 212 to receive cross post 80. A concavely curved outer surface portion 208 extends between raised ends 210. The spinous processes are positionable in concavely curved outer surface portion 208 and received between raised ends 210. The nested arrangement provides increased surface area of contact between spacer member 200 and the spinous processes, distributing loading exerted on the spinous processes over correspondingly greater surface areas.

Figure 19:
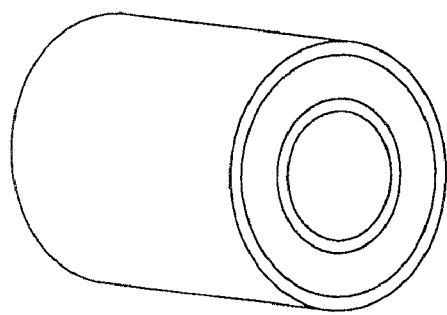
FIG. 19 is a perspective view of another embodiment spacer member.
Figure 20:
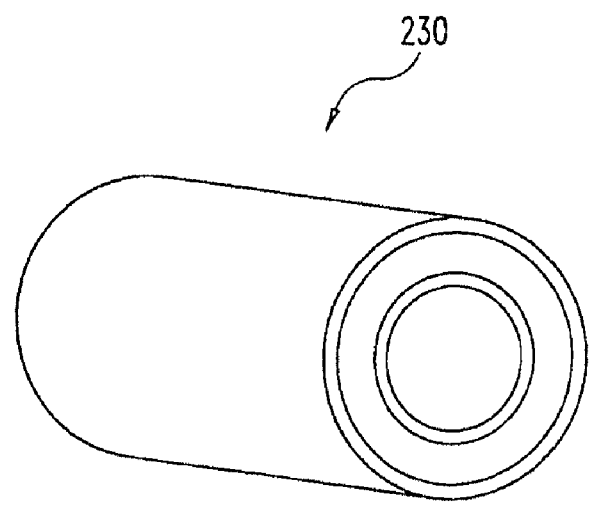
FIG. 20 is a perspective view of another embodiment spacer member.

FIGS. 19 and 20 show spacer member 220, 230 that are similar to the spacer members 70, 170 of FIGS. 15 and 16, respectively. However, the passages do not include a keyed portion, allowing the spacer members 220, 230 to rotate about cross post 80. It is also contemplated that the spacer member embodiments 180 and 200 in FIGS. 17 and 18 can have passages with keyed portions or without keyed portions, depending whether or not it is desired to have the spacer member rotatable about the cross post 80. The rotatable spacer members facilitate the spacer member maintaining a bearing relationship with the adjacent spinous process surfaces without twisting or binding as the spinous processes move relative to the spacer member.

Figure 21:
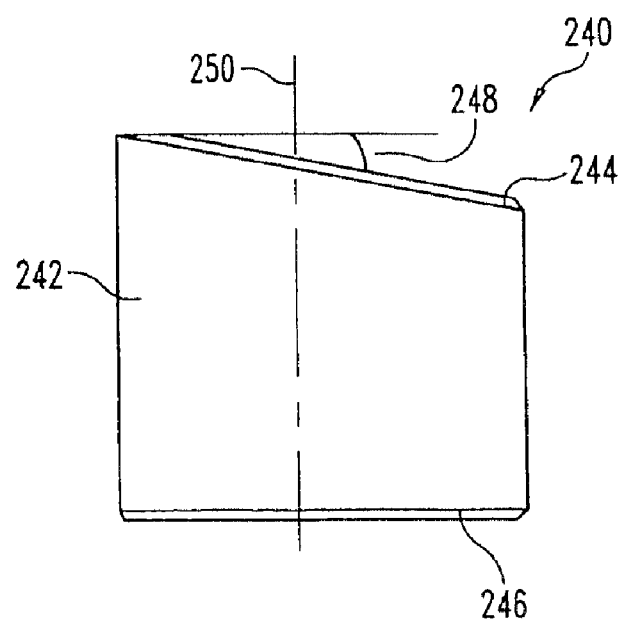
FIG. 21 is an elevation view of another embodiment spacer member.

FIG. 21 shows a spacer member 240 having a cylindrical body 242 extending between a first end 244 and a second end 246. A passage (not shown) can be provided along spacer member 240 between ends 244, 246. End 244 can be angled relative to central axis 250 at an angle 248. Spacer member 240 with the angled end can be employed in procedures where one of the plates 30, 50 is angled relative to the other to accommodate the spinous process anatomy. The angled end or ends can conform to and maintain contact with the clamping surfaces or surfaces of the plate or plates. Such contact can prevent or resist longitudinal movement of the spacer member along cross post 80 and prevent the formation of gaps between the spacer member and the plates.

It is contemplated that a number of spacer members 240 can be provided in a set having various angles 248 at one or both ends. The surgeon can select the spacer member from the set providing the desired angulation and fit between plates 40, 50 based on pre-operative planning or conditions encountered during surgery.

It is contemplated that any of the spacer member embodiments can be provided in various sizes from which a desired spacer member size and/or shape can be selected by the surgeon. The spacer members can be provided in a kit or as a set, and the spacer member providing the desired outer surface profile and size is selected for placement between the spinous processes based on pre-operative planning or conditions encountered during surgery.

It is further contemplated that the spacer members can be made from a rigid material that positively prevents extension motion of the spinous processes. In another embodiment, the spacer member is made from a compressible material to allow at least limited spinal extension motion between the spinous processes. In still another embodiment, the spacer member is made from an expandable material or is an expandable device that positively directs distraction forces between the spinous processes. In a further embodiment, the spacer member is compressible to initially fit between the spinous processes, and resiliently expands to positively exert a distraction force while yielding under compression forces to allow at least limited spinal extension motion.

In use, the device can be implanted for posterior spinal stabilization as a stand-alone procedure or in conjunction with other procedures. The device can be positioned through a small posterior incision in the patient of sufficient size to admit the device and instrumentation. Following the incision, muscle is moved aside if and as needed for placement of the device into position between spinous processes. After the spacer member is positioned between the spinous processes, the locking member can be loosened if necessary and the plates pushed toward one another with a compression instrument or manually. If spikes are provided, compression is continued until the spikes are sufficiently engaged to the bony material of the spinous processes. The angulation of first plate 30 relative to cross post 80 can be sufficient to enable adaptation of the device to different thicknesses and shapes of the spinal processes of adjacent vertebrae.

Following engagement of plates 30, 50 on the spinal processes, locking member 90 is tightened onto cross post 80 using an appropriate instrument. Locking member 90 may be provided with a break-off portion that provides an indication when sufficient torque is applied. Plates 30, 50 are clamped into engagement with the spinous processes, maintaining the alignment and spacing of the spinous processes while also providing resistance to spinal extension and flexion. The spacer member between the spinous processes can contact and provide support of the adjacent inferior and support spinous process surfaces, resisting settling and compression of the space between the spinous processes. The spacer member can be rigid or stiff so that extension motion is prevented. In another form, the spacer member is resiliently compressible to allow at least limited extension motion. During the implantation procedure, the surgeon can select the shape and size of the spacer member that provides the desired contact or fit with the adjacent spinous processes based on the conditions learned of during pre-operative planning or encountered during surgery.

While the invention has been illustrated and described in detail in the drawings and foregoing description, the same is to be considered as illustrative and not restrictive in character.

All changes and modifications that come within the spirit of the invention are desired to be protected.

What is claimed is:

1. A spinal implant comprising:
   a first plate having a medial face configured to confront adjacent spinous processes;
   a second plate having a medial face configured to confront the adjacent spinous processes; said second plate disposed in spaced relation to said first plate;
   a post connecting the second plate to the first plate and extending along a longitudinal post axis oriented transverse to the medial face of the second plate;
   the second plate having a first bore passing through the medial face of the second plate generally normal thereto; the post extending from the medial face of the first plate such that the post longitudinal axis is aligned to extend through the first bore;
   wherein the medial faces of each of the plates extend from the post in opposite directions therefrom between a cephalad end of the respective plate that is positionable along a cephaladly located spinous process and a caudal end of the respective plate positionable along a caudally located spinous process;
   wherein the medial face of the first plate comprises a first plurality of inwardly projecting projections that extend generally toward the second plate in both a cephalad section thereof and a caudal section thereof;
   wherein the medial face of the second plate comprises a second plurality of inwardly projecting projections that extend generally toward the first plate in both a cephalad section thereof and a caudal section thereof;
   wherein the first plate is curvedly configured such that a first theoretical line connecting a first side-edge of the first plate in the cephalad end of the first plate and the first side-edge of the first plate in the caudal end is spaced outwardly from the first side-edge of the first plate proximate the post;
   wherein the second plate is curvedly configured such that a second theoretical line connecting a second side-edge of the second plate in the cephalad end of the second plate and the second side-edge of the second plate in the caudal end is spaced outwardly from the second side-edge of the second plate proximate the post;
   a resiliently deformable spacer having a longitudinal spacer axis and a passage extending along the longitudinal spacer axis; the spacer positioned about the post and disposed between the first and second plates with the post extending through the passage; the spacer distinct from both the first and second plates;
   a locking mechanism distinct from the spacer and operative to secure the second plate in position relative to the post;
   wherein the second plate is moveable along the post toward the first plate and lockable at an infinite number of positions relative thereto via engagement of the locking mechanism with the post.

2. The spinal implant of claim 1 wherein the post is pivotable relative to the first plate about a pivot axis; the pivot axis located opposite the second plate with respect to the medial face of the first plate; the pivot axis oriented normal to a theoretical plane disposed generally perpendicular to the medial face of the first plate and containing the longitudinal post axis; the post pivotable about the pivot axis such that the first and second plates may thereby be displaced relative to each other in a direction lying in the theoretical plane and transverse to the post longitudinal axis.

3. The spinal implant of claim 1 wherein the medial faces of the first and second plates are configured to be generally mirror images of each other with respect to a plane perpendicular to the post longitudinal axis and disposed midway between the medial faces of the first and second plates.

4. The spinal implant of claim 1 wherein the spacer is rotatable about the post longitudinal axis.

5. The spinal implant of claim 1 wherein the spacer is non-rotatably positioned about the post.

6. The spinal implant of claim 1 wherein the first and second plates are unconnected to each other by other portions of the implant except through the post, spacer, and locking mechanism.

7. The spinal implant of claim 1 wherein the spacer abuts the medial faces of both the first and second plates.

8. The spinal implant of claim 1 wherein the first bore has a bore axis disposed generally normal to the medial face of the second plate; and wherein the post extends from the medial face of the first plate such that the post longitudinal axis is aligned to extend through the first bore coincident with the bore axis and generally perpendicular to the medial face of the first plate.

9. The spinal implant of claim 1 wherein the spacer has a cross-section shape normal to post longitudinal axis with a generally flat section and outwardly convex sections disposed on opposing sides of the generally flat section.

10. The spinal implant of claim 1 wherein the spacer extends along a central axis between opposite ends thereof, the opposite ends being located adjacent a respective one of the first and second plates, wherein at least one of the opposite ends is angled relative to the other of the opposite ends.

11. The spinal implant of claim 1 wherein the first plate is configured such that a theoretical line connecting an anterior edge of the cephalad end of the first plate and an anterior edge of the caudal end of the first plate is spaced outwardly from an anterior edge of the first plate proximate the post.

12. A spinal implant comprising:
   a first plate having a medial face configured to confront adjacent spinous processes;
   a second plate having a medial face configured to confront the adjacent spinous processes; said second plate disposed in spaced relation to said first plate;
   a post connecting the second plate to the first plate and extending along a longitudinal post axis oriented transverse to the medial face of the second plate;
   the second plate having a first bore passing through the medial face of the second plate generally normal thereto; the post extending from the medial face of the first plate such that the post longitudinal axis is aligned to extend through the first bore;
   wherein the medial faces of each of the plates extend from the post in opposite directions therefrom between a cephalad end of the respective plate that is positionable along a cephaladly located spinous process and a caudal end of the respective plate positionable along a caudally located spinous process;
   wherein the medial face of the first plate comprises a first plurality of inwardly projecting projections that extend generally toward the second plate in both a cephalad section thereof and a caudal section thereof;
   wherein the medial face of the second plate comprises a second plurality of inwardly projecting projections that extend generally toward the first plate in both a cephalad section thereof and a caudal section thereof;
   a spacer having a longitudinal spacer axis and a bore extending along the longitudinal spacer axis; the spacer rotatably positioned about the post and disposed between the first and second plates with the post extending through the bore; the spacer distinct from both the first and second plates; the spacer having an external surface;

a locking mechanism distinct from the spacer and operative to secure the second plate in position relative to the post;

wherein the second plate is moveable along the post toward the first plate and lockable at an infinite number of positions relative thereto via engagement of the locking mechanism with the post;

wherein the spacer external surface is configured to abut the spinous processes when the implant is disposed between the spinous processes with the medial faces of the first and second plates confronting the spinous processes and the post extending through a sagittal plane defined by the spinous processes.

13. The spinal implant of claim 12 wherein the spacer is resiliently deformable in a plane normal to the bore.

\* \* \* \* \*